US011769584B2

(12) United States Patent
Sin Kwok Wong et al.

(10) Patent No.: US 11,769,584 B2
(45) Date of Patent: *Sep. 26, 2023

(54) FACE REATTACHMENT TO BRAIN IMAGING DATA

(71) Applicant: Omniscient Neurotechnology Pty Limited, Sydney (AU)

(72) Inventors: Bryan Sin Kwok Wong, Toronto (CA); Michael Edward Sughrue, Sydney (AU); Stephane Philippe Doyen, Glebe (AU); Jacob David Roberts, Encinitas, CA (US)

(73) Assignee: Omniscient Neurotechnology Pty Limited, Sydney (AU)

(*) Notice: Subject to any disclaimer, the term of this patent is extended or adjusted under 35 U.S.C. 154(b) by 129 days.

This patent is subject to a terminal disclaimer.

(21) Appl. No.: 17/481,277

(22) Filed: Sep. 21, 2021

(65) Prior Publication Data

US 2022/0005585 A1  Jan. 6, 2022

Related U.S. Application Data

(63) Continuation of application No. 17/238,140, filed on Apr. 22, 2021, now Pat. No. 11,145,404.

(Continued)

(51) Int. Cl.
| | |
|---|---|
| G06K 9/00 | (2022.01) |
| G16H 10/20 | (2018.01) |
| G16H 30/20 | (2018.01) |
| G06T 7/00 | (2017.01) |
| G06T 11/00 | (2006.01) |
| G06F 9/455 | (2018.01) |
| A61B 5/00 | (2006.01) |

(Continued)

(52) U.S. Cl.
CPC .......... *G16H 30/20* (2018.01); *A61B 5/0013* (2013.01); *A61B 5/0022* (2013.01); *A61B 5/4064* (2013.01); *G06F 9/451* (2018.02); *G06F 9/45558* (2013.01); *G06T 7/0012* (2013.01); *G06T 11/00* (2013.01); *G16H 10/60* (2018.01); *G16H 30/40* (2018.01); *H04L 9/32* (2013.01); *H04L 63/0428* (2013.01); *G06T 2207/20092* (2013.01); *G06T 2207/30016* (2013.01)

(58) Field of Classification Search
CPC .......... G06K 9/00; G06Q 50/00; G16H 10/20
USPC ........ 382/100, 103, 106, 112–115, 128–134, 382/155, 168, 173, 181, 189, 206, 219, 382/224, 232, 254, 276, 285–295, 382/305–306, 312, 235; 705/3
See application file for complete search history.

(56) References Cited

U.S. PATENT DOCUMENTS

| | | |
|---|---|---|
| 2008/0021834 A1 | 1/2008 | Holla et al. |
| 2008/0077604 A1 | 3/2008 | Bharara |

(Continued)

FOREIGN PATENT DOCUMENTS

EP  3282379  2/2018

OTHER PUBLICATIONS

International Search Report and Written Opinion in International Appln. No. PCT/AU2021/050573, dated Sep. 17, 2021, 12 pages.

*Primary Examiner* — Seyed H Azarian
(74) *Attorney, Agent, or Firm* — Fish & Richardson P.C.

(57) ABSTRACT

A cloud computing system is described that communicates with a virtual machine to reattach the face of a patient to brain imaging data before the brain imaging data is transmitted for display on a brain navigation system.

20 Claims, 13 Drawing Sheets

Related U.S. Application Data

(60) Provisional application No. 63/038,400, filed on Jun. 12, 2020.

(51) Int. Cl.
  *H04L 9/32* (2006.01)
  *G16H 10/60* (2018.01)
  *G16H 30/40* (2018.01)
  *G06F 9/451* (2018.01)
  *H04L 9/40* (2022.01)

(56) References Cited

U.S. PATENT DOCUMENTS

| | | |
|---|---|---|
| 2009/0041329 A1 | 2/2009 | Nordell et al. |
| 2011/0153351 A1 | 6/2011 | Vesper et al. |
| 2013/0208955 A1* | 8/2013 | Zhao ................ G16Z 99/00 382/128 |
| 2014/0087342 A1 | 3/2014 | Campanatti et al. |
| 2015/0237106 A1 | 8/2015 | Golay |
| 2016/0004820 A1* | 1/2016 | Moore ................ G16H 15/00 705/3 |
| 2016/0147954 A1* | 5/2016 | Ng Tari ............. G16H 40/20 705/3 |
| 2016/0317077 A1* | 11/2016 | Sillay ................ A61B 5/1101 |
| 2019/0027244 A1* | 1/2019 | Wu ..................... G16H 30/20 |
| 2019/0156921 A1* | 5/2019 | Kohli ................. G06F 16/93 |
| 2019/0287686 A1 | 9/2019 | Takeda |

\* cited by examiner

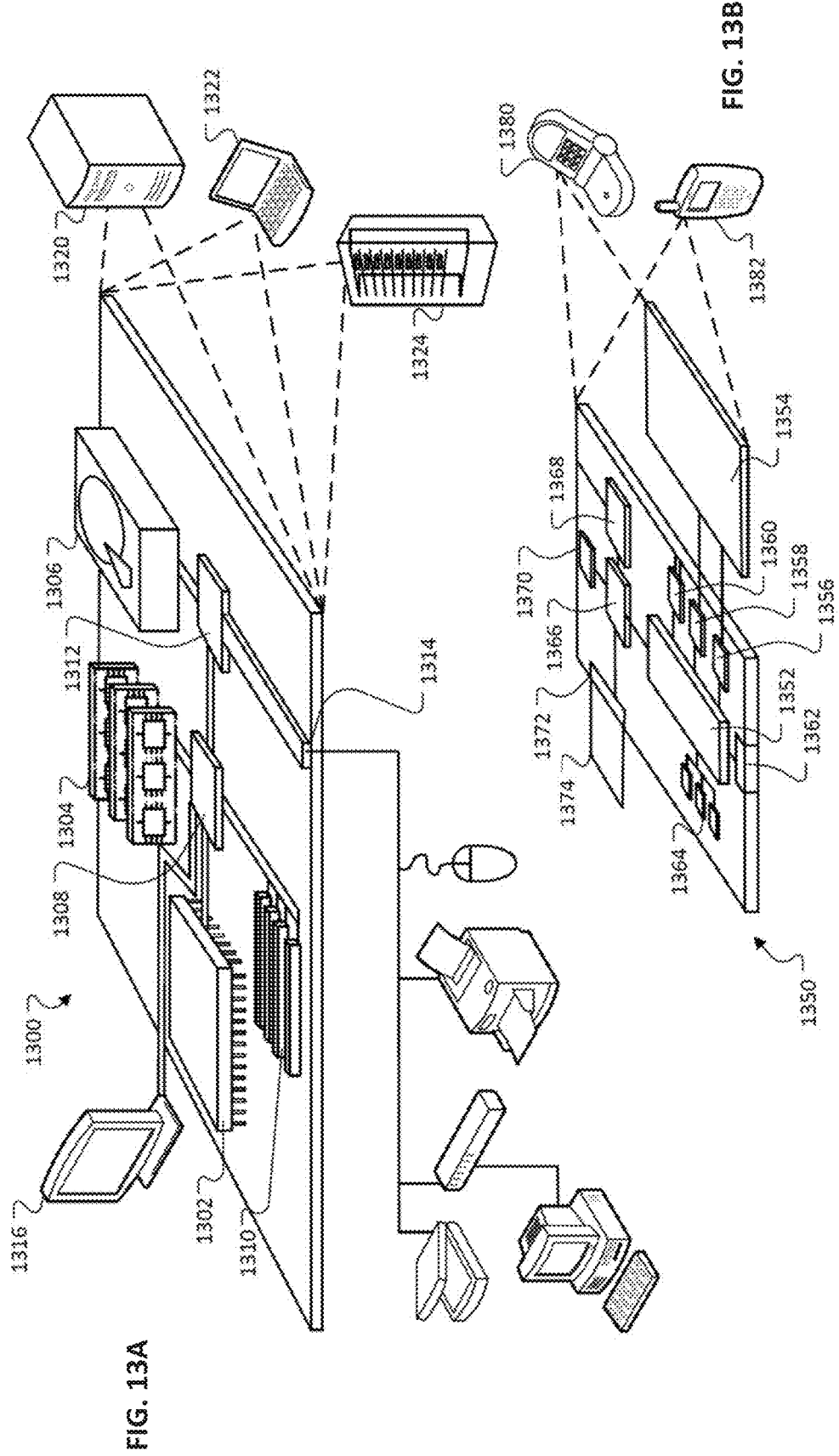

FACE REATTACHMENT TO BRAIN IMAGING DATA

RELATED APPLICATION

This application is a continuation of U.S. application Ser. No. 17/238,140, filed Apr. 22, 2021, which claims benefit of and priority to U.S. Provisional Patent Application Ser. No. 63/038,400, entitled "Clinical Infrastructure with Features for the Prevention of Egress of Private Information," filed Jun. 12, 2020, the entire contents of which are incorporated herein by reference.

TECHNICAL FIELD

The subject matter described herein relates to a cloud computing system that communicates with a virtual machine to reattach the face of a patient to brain imaging data before the brain imaging data is transmitted for display on a brain navigation system.

BACKGROUND

Medical imaging includes the technique and process of creating visual representations of the interior of a body for clinical analysis and medical intervention, as well as visual representation of physiology of some organs or tissues. Medical imaging seeks to reveal internal structures hidden by the skin and bones, as well as to diagnose and treat disease. Medical imaging also establishes a database of normal anatomy and physiology to make it possible to identify abnormalities.

SUMMARY

Cloud based solutions are implemented to provide medical imaging data to brain navigation systems. Compliance requirements often require or encourage removal of personal health information (PHI), including the patient's face, from the medical imaging data prior to transmitting such data outside the hospital information technology infrastructure. Such removal of PHI, specifically face, renders the medical imaging data as anonymous, which make it difficult for a clinician to identify the patient while reviewing the medical imaging data. To ensure a clinician can treat a patient using the patient's medical imaging data, it is crucial that the patient's PHI, which was removed from the medical imaging data, is reattached to the medical imaging data before transmitting the data. While the reattachment of PHI is helpful, the clinicians can benefit even more if the face is also reattached to the medical imaging data, especially because many clinicians are able to quickly identify their patients through the patients' faces. This disclosure focuses, among other things, on reattachment of the face to the medical imaging data. The reattachment of the face is performed in a temporary storage—and in some implementations a random access memory (RAM)—to prevent any potential interception of the face while the face is being reattached. The reattachment of the PHI is performed outside the cloud computing system (e.g. at a gap server within the hospital IT infrastructure) to prevent any potential interception of the PHI while the PHI is being reattached.

In one aspect, a cloud computing system can receive, from a remote computer, data indicative of brain imaging objects selected by a user. The cloud computing system can retrieve, from a gap server in response to receiving the data indicative of the selected brain imaging objects, brain images and first metadata with anonymous identifiers and face data but without personal health information (PHI). The cloud computing system can obtain, from a database within the cloud computing system storing processed data and based on the data indicative of the selected brain imaging objects, a portion of the processed data that has the brain images and second metadata with anonymous identifiers but without the PHI and without the face data. The cloud computing system can generate, based on the retrieved brain images and first metadata and the portion of the processed data that has the brain images and second metadata, the brain images with third metadata with anonymous identifiers and the face data but without the PHI. The brain images with the third metadata can be indicative of the data indicative of the selected brain imaging objects. The cloud computing system can transmit the brain images with the third metadata with the anonymous identifiers and the face data but without the PHI to the gap server.

In some implementations, one or more of the following can additionally be implemented either individually or in any feasible combination. The gap server can implement a PHI attachment module that attaches PHI to the brain images with the third metadata with the anonymous identifiers and the face data. The gap server can transmit the brain images with the anonymous identifiers and the face data and PHI to a picture archiving and communication system (PACS). The PACS can transmit the brain images with the anonymous identifiers and the face data and PHI to a brain navigation system. The received data indicative of the selected brain imaging objects can be encrypted prior to the receiving of the data indicative of the selected brain imaging objects. The received encrypted data can be decrypted prior to the retrieving of the brain images and the first metadata from the gap server. The generating of the brain images with the third metadata and the face data can include attaching the face data to the brain images in a temporary storage of the cloud computing system. The cloud computing system can prevent the PHI or the face data from being saved in a database of the cloud computing system. The data indicative of the selected brain imaging objects can include one or more of a tract or a parcellation selected from a plurality of objects. The brain images with the third metadata with the anonymous identifiers and the face data but without the PHI can be encrypted prior to the transmitting of the third metadata with the anonymous identifiers and the face data but without the PHI to the gap server. The processed data stored in the database can be without the PHI and without the face data. The face data can be removed by the cloud computing system prior to generation of the processed data.

In another aspect, one or more non-transitory computer program products are described that can store instructions that, when executed by at least one programmable processor, cause the at least one programmable processor to perform operations comprising one or more of: receiving, from a remote computer, data indicative of brain imaging objects selected by a user; retrieving, from a gap server in response to receiving the data indicative of the selected brain imaging objects, brain images and first metadata with anonymous identifiers and face data but without personal health information (PHI); obtaining, from a database storing processed data and based on the data indicative of the selected brain imaging objects, a portion of the processed data that has the brain images and second metadata with anonymous identifiers but without the PHI and without the face data; generating, based on the retrieved brain images and first metadata and the portion of the processed data that has the brain images and second metadata, the brain images with third metadata with anonymous identifiers and the face data but without the PHI, wherein the brain images with the third metadata are indicative of the data indicative of the selected brain imaging objects; and transmitting the brain images with the third metadata with the anonymous identifiers and the face data but without the PHI to the gap server.

In some implementations, one or more of the following can additionally be implemented either individually or in any feasible combination. The gap server can implement a PHI attachment module that attaches PHI to the brain images with the third metadata with the anonymous identifiers and the face data. The gap server can transmit the brain images with the anonymous identifiers and the face data and PHI to a picture archiving and communication system (PACS). The PACS can transmit the brain images with the anonymous identifiers and the face data and PHI to a brain navigation system. The received data indicative of the selected brain imaging objects can be encrypted prior to the receiving of the data indicative of the selected brain imaging objects. The received encrypted data can be decrypted prior to the retrieving of the brain images and the first metadata from the gap server. The generating of the brain images with the third metadata and the face data can include attaching the face data to the brain images in a temporary storage of the cloud computing system. The cloud computing system can prevent the PHI or the face data from being saved in a database of the cloud computing system. The data indicative of the selected brain imaging objects can include one or more of a tract or a parcellation selected from a plurality of objects. The brain images with the third metadata with the anonymous identifiers and the face data but without the PHI can be encrypted prior to the transmitting of the third metadata with the anonymous identifiers and the face data but without the PHI to the gap server. The processed data stored in the database can be without the PHI and without the face data. The face data can be removed by the cloud computing system prior to generation of the processed data.

In yet another aspect, a system is described that can include at least one programmable processor, and a machine-readable medium storing instructions that, when executed by the at least one programmable processor, cause the at least one programmable processor to perform operations including: receiving, from a remote computer, data indicative of brain imaging objects selected by a user; retrieving, from a gap server in response to receiving the data indicative of the selected brain imaging objects, brain images and first metadata with anonymous identifiers and face data but without personal health information (PHI); obtaining, from a database storing processed data and based on the data indicative of the selected brain imaging objects, a portion of the processed data that has the brain images and second metadata with anonymous identifiers but without the PHI and without the face data; generating, based on the retrieved brain images and first metadata and the portion of the processed data that has the brain images and second metadata, the brain images with third metadata with anonymous identifiers and the face data but without the PHI, wherein the brain images with the third metadata are indicative of the data indicative of the selected brain imaging objects; and transmitting the brain images with the third metadata with the anonymous identifiers and the face data but without the PHI to the gap server.

In some implementations, one or more of the following can additionally be implemented either individually or in any feasible combination. The gap server can implement a PHI attachment module that attaches PHI to the brain images with the third metadata with the anonymous identifiers and the face data. The gap server can transmit the brain images with the anonymous identifiers and the face data and PHI to a picture archiving and communication system (PACS). The PACS can transmit the brain images with the anonymous identifiers and the face data and PHI to a brain navigation system. The received data indicative of the selected brain imaging objects can be encrypted prior to the receiving of the data indicative of the selected brain imaging objects. The received encrypted data can be decrypted prior to the retrieving of the brain images and the first metadata from the gap server. The generating of the brain images with the third metadata and the face data can include attaching the face data to the brain images in a temporary storage of the cloud computing system. The cloud computing system can prevent the PHI or the face data from being saved in a database of the cloud computing system. The data indicative of the selected brain imaging objects can include one or more of a tract or a parcellation selected from a plurality of objects. The brain images with the third metadata with the anonymous identifiers and the face data but without the PHI can be encrypted prior to the transmitting of the third metadata with the anonymous identifiers and the face data but without the PHI to the gap server. The processed data stored in the database can be without the PHI and without the face data. The face data can be removed by the cloud computing system prior to generation of the processed data.

The subject matter described herein provides many advantages. For example, the cloud computing system generates medical imaging data that is useful for a clinician while preserving security and privacy of the medical imaging data in line with compliance requirements. More particularly, the cloud computing system enables reattachment of face of a patient to the medical imaging data before that medical imaging data is presented (e.g. output, provided or displayed) to the clinician so that the clinician can promptly identify the patient for whom the medical imaging data is being displayed. Such reattachment can save a lot of inconvenience and time for the clinician. In addition, the cloud computing system performs the reattachment in a temporary storage (and/or the random access memory (RAM) in some implementations) to prevent any potential interception of private or secure information of a patient while the face is being reattached, thereby preserving patient privacy and complying with regulations for maintaining privacy of patients.

The details of one or more variations of the subject matter described herein are set forth in the accompanying drawings and the description below. Other features and advantages of the subject matter described herein will be apparent from the description, drawings, and claims.

BRIEF DESCRIPTION OF DRAWINGS

FIGS. 13A and 13B are schematic diagrams that show examples of a computing device and a mobile computing device, respectively.

Like reference symbols in various drawings indicate like elements.

DETAILED DESCRIPTION

Figure 1:
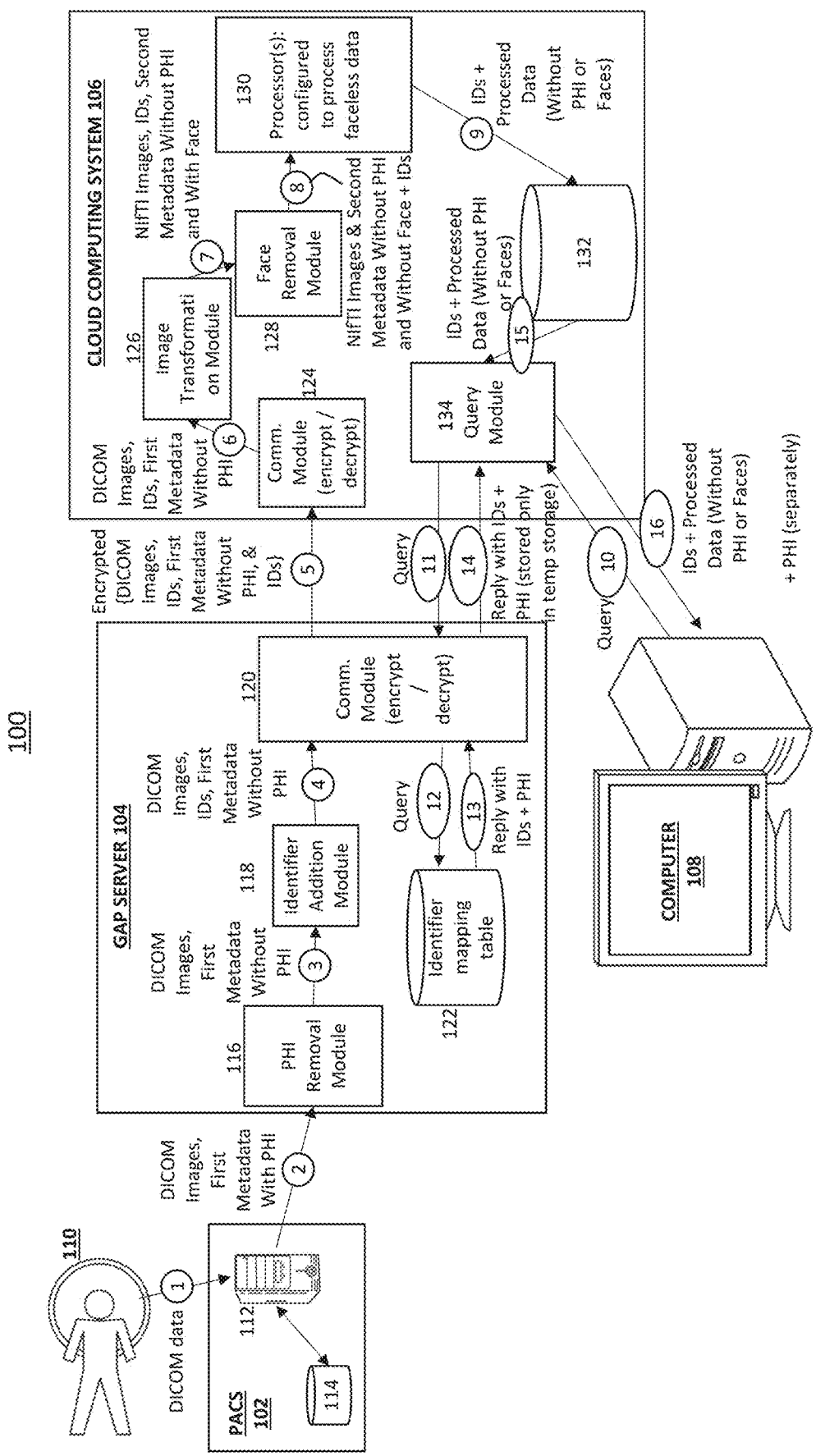
FIG. 1 illustrates a computing landscape that includes a cloud computing system to process brain imaging data, store brain imaging data, facilitate querying of the stored data, and transmit—in response to the querying—stored data as well as respective PHI corresponding to the brain imaging data.

FIG. 1 illustrates a computing system 100 for receiving medical images, processing those medical images in accordance with compliance requirements, and outputting results of the processing to a clinician. The computing system 100 can include (a) a hospital information technology infrastructure that can include (i) a picture archiving and communication system (PACS) 102, and (ii) a gap server 104, (b) a cloud computing system 106, and (c) a computer 108 configured to be operated by a clinician. The hospital information technology infrastructure can be confined to a single location in some implementations, and in other implementations may be distributed across multiple geographically separated locations.

Picture Archiving and Communication System (PACS) 102

PACS 102 is a computing system that can receive, at step 1, medical imaging data from an imaging device 110, extract medical images (e.g. Digital Imaging and Communications in Medicine (DICOM) images) and related first metadata from the received medical imaging data, store the medical images and related first metadata in a storage (e.g. database), and transmit, at step 2, at least some of the stored data for further processing to the gap server 104. The imaging device 110 can be a magnetic resonance imaging (MRI) machine, X-ray machine, computed tomography (CT) machine, positron emission tomography (PET) machine, or the like. The PACS 102 can include at least one programmable processor 112, and at least one non-transitory machine-readable medium 114 storing instructions that, when executed by the at least one programmable processor 112, can cause the at least one programmable processor 112 to perform various operations described herein. The non-transitory machine-readable medium 114 can include one or more databases and/or memory that can store the medical images and related metadata. The extracted medical images (e.g. DICOM images) and related first metadata that are stored in PACS 102 include protected health information (PHI).

First metadata is metadata associated with each image. Metadata for each image is information that describes that image. Such metadata can embedded in the beginning of the image file as a header, in DICOM tags, or in pixel data related to the DICOM images. Metadata can include one or more of at least the following: (1) data about the image, such as image matrix dimensions, the spatial resolution, the pixel depth, the photometric interpretation, or the like, (2) data identifying the imaging device 110, such as make and model of the imaging device 110, location of the imaging device 110, or the like, (3) data indicating how the image was produced by the imaging device 110, such as data indicating how the image was produced, such as parameters related to the pulse sequence used by the imaging device 110, e.g. timing data, flip angle, number of acquisitions by the imaging device 110, and (4) PHI, which can be identification data associated with the medical image, such as patient identification by way of name, address, birth date, social security number, medical and laboratory reports, physician name, hospital name, and date of examination.

The use of PACS 102 is technologically advantageous in radiology departments and practices, both large and small. Traditionally, the radiology department has been constrained in terms of efficiency and cost by the process of dark room processing, storage of radiology films, copying of radiology films, and the process of manual review of the radiology films by clinicians. PACS 102 offers many technological and other advantages over such traditional implementations. For example, PACS 102 digitizes and distributes medical imaging data in the digital format, which effectively gives clinicians the ability to remotely access the images at any time, which in turn helps the clinicians to manage their time more effectively. Further, PACS 102 reduces the cost of radiology by eliminating the need to have hardcopy films and the associated physical storage space required for storing those films. Moreover, PACS 102 provides a faster and more reliable way of retrieving prior images. Additionally, PACS 102 provides for easy integration of images into the information technology (IT) systems of clinics or hospitals, which enables an effective way of managing comprehensive patient information and providing of a single point of access for all patient information. Also, the digital transmission of images and reports can enable a quicker generation of patient reports, which can enable a fast diagnosis result, which in turn enhances patient care. Further, PACS 102 can facilitate compliance with various laws, including privacy laws (e.g. Health Insurance Portability and Accountability Act, also known by the acronym HIPAA) that stipulate how PHI should be protected from fraud and theft.

The format for medical images generally described herein is Digital Imaging and Communications in Medicine (DICOM), as DICOM is the universal format for image storage and transfer by PACS. The DICOM format specifies protocols for image exchange or transmission, image compression, three dimensional (3-D) visualization, image presentation, and reporting of results. For the DICOM format, the header can have a variable length binary format, the extension can be .dcm, and the data types can include signed or unsigned integer (8-bit; 16-bit; or 32-bit only allowed for a radiotherapy dose), and float may or may not be supported. While the extension .dcm has been described, in some implementations the DICOM file may not have an extension or may have any other extension, such as .ima.

Gap Server 104

The gap server 104 can receive, from PACS 102, the medical images (e.g. DICOM images) along with the first metadata. The gap server 104 can be one or more virtual machines coupled with one or more containers. A virtual machines (VM) is an abstraction of physical hardware that can turn one server into many servers. A hypervisor can allow multiple VMs to run on a single machine. Each VM includes a full copy of an operating system, the application, necessary binaries and libraries, which can take up tens of gigabytes (GBs). A containers is an abstraction at the application layer that packages code and dependencies together. Multiple containers can run on the same machine and share an operating system (OS) kernel with other containers, each running as isolated processes in user space. Containers take up less space than VMs (as container images are typically tens of megabytes (MBs) in size), can handle more applications and require fewer VMs and operating systems. A container can be a lightweight, standalone, executable package of software that includes everything needed to run an application, including code, runtime, system tools, system libraries and settings. Container is referred to as lightweight because containers share the virtual machine's OS system kernel and therefore do not require an OS per application, driving higher server efficiencies and reducing server costs. Containers and virtual machines have similar resource isolation and allocation benefits, but function differently because containers virtualize the operating system instead of hardware. Containers and VMs are used together here so as to provide significant flexibility in deploying and managing an application that displays brain imaging data.

The gap server 104 can have specific hardware, software and networking requirements. In various examples, the gap server 104 may have any combination of the following requirements or any variation thereof. In a specific implementation, the hardware requirements can include a VM with a disk space of 300 gigabytes (GB), random access memory (RAM) of at least 8 GB, and a processor with 4 cores at 2 gigahertz (GHz). The software requirements can include an agnostic operating system (i.e. software can run under any operating system), and the installation of the gap server 102 can be a container.

The networking requirements of the gap server 104 can include (a) networking requirements for inbound data from PACS 102, (b) networking requirements for outbound data to PACS 102, (c) networking requirements for inbound data from cloud computing system 106, and (d) networking requirements for outbound data to cloud computing system 106. The networking requirements can specify the port and protocol of data to be transmitted. In specific examples, the port specified by the networking requirements for exchange of data with the PACS 102 can be a port that enables data exchange using Transmission Control Protocol (TCP), which is a standard that defines how to establish and maintain a network conversation through which application programs can exchange data. The protocol specified by the networking requirements for exchange of data with the PACS 102 can be DICOM C-STORE protocol based on Service Class User (SCU) and Service Class Provider (SCP) only. The protocol specified by the networking requirements for exchange of data with the cloud computing system 106 can be Hypertext Transfer Protocol (HTTP), where the communication protocol is encrypted using Transport Layer Security (TLS).

The gap server 104 can include a physical gateway that may allow only some of the entire data within the hospital IT network where the PACS 102 and the gap server 104 reside, which in turn reduces the data load processed by the gap server 104, thereby allowing faster processing by, and requiring lower storage requirements on, the gap server 104.

The gap server 104 can implement a PHI removal module 116, an identifier addition module 118, a communication module 120, and an identifier mapping table 122. The term module, as noted herein, can include software instructions and codes to perform a designated task or a function. A module as used herein can be a software module or a hardware module, each of which can be related to a container or VM, as explained above. A software module can be a part of a computer program, which can include multiple independently developed modules that can be combined or linked via a linking module. A software module can include one or more software routines. A software routine is computer readable code that performs a corresponding procedure or function. A hardware module can be a self-contained component with an independent circuitry that can perform various operations described herein.

The PHI removal module 116 can receive, at step 2, the DICOM images and first metadata, including the PHI from the at least one processor 112 of PACS 102. The PHI removal module can remove the PHI from the received data. PHI is removed at the gap server 100 to comply with compliance requirements, which require or encourage removal of PHI from the medical imaging data prior to transmitting such data outside the hospital IT infrastructure, which includes the PACS 102 and gap server 104. Such compliance requirements are generally designed to preserve patient privacy. The PHI removal module 116 outputs, at step 3, the DICOM images and first metadata without the PHI.

The identifier addition module 118 adds anonymous IDs to the DICOM images and first metadata without the PHI. The addition of anonymous IDs advantageously allows tracking of images with respective PHI. The anonymity of data allows maintaining patient privacy and compliance with compliance requirements.

The communication module 120 encrypts the data in accordance with networking requirements discussed above. The communication module 120 receives, at step 4, the DICOM images and first metadata without the PHI, encrypts the received data, and transmits, at step 5, the encrypted data over a communication network to the cloud computing system 106.

Cloud Computing System 106

The cloud computing system 106 is generally configured to receive imaging data from the hospital IT infrastructure, process the imaging data, store the processed data, facilitate querying of the processed data from a remote computer, and transmit—in response to the querying—query result along with respective PHI to the querying computer that can display the query result to e.g. a clinician.

The use of the cloud computing system 106 here is advantageous because it prevents the hospital IT infrastructure from the complexity of performing the data processing (as described herein) performed by the cloud computing system 106. In turn, a provider of the cloud computing system 106 can benefit from significant economies of scale by performing same or similar brain image processing for IT systems of many respective hospitals or clinics. The cloud computing system 106 can facilitate a service—to IT systems of hospitals or clinics—of data processing of brain images in the form of one or more of a software-as-a-service (SaaS), infrastructure-as-a-service (IaaS), and platform-as-a-service (PaaS).

The cloud computing system 106 can include a communication module 124, an image transformation module 126, a face removal module 128, one or more processors 130 configured to process faceless data (so as to comply with compliance or legal requirements), a database 132 storing the processed data, and a query module 134.

The communication module 124 can receive, at step 5 from the communication module 120, encrypted DICOM images and first metadata without PHI along with anonymous IDs. The communication module 124 can decrypt the received data to obtain DICOM images and first metadata without PHI along with anonymous IDs.

The image transformation module 126 can receive, at step 6, the DICOM images and first metadata without PHI along with anonymous IDs from the communication module 124. The image transformation module 126 can transform the DICOM images and first metadata without PHI along with anonymous IDs to Neuroimaging Informatics Technology Initiative (NIfTI) images and second metadata without PHI and with face along with anonymous IDs.

Images in the DICOM format are transformed to images with NIfTI because while the DICOM format is intended to generally standardize the images generated by various diagnostic modalities, the NIfTI format is more effective for processing and analyzing imaging data where the imaging data can have multiple different data formats such as in the case of functional magnetic resonance imaging (fMRI). The NIfTI format has the following characteristics: (a) a header that generally has a fixed-length of 352 byte binary format (348 byte in the case of data stored as .img and .hdr), but the header can be extended in some cases, (b) extension of .nii, and (c) data type of signed and unsigned integer (from 8-bit to 64-bit), float (from 32-bit to 128-bit), or complex (from 64-bit to 256-bit).

The second metadata is related to, and created from, the first metadata. The second metadata is created from the first metadata because the NIfTI header is different from the DICOM header, and cannot contain all the data contained in the DICOM header. For example, the DICOM header contains various scan parameters—e.g. .bval file parameters, .bvec file parameters, repetition time, flip angle, and/or the like—that are not saved to the NIfTI file (and these parameters may be extracted into separate files as relevant or needed). The NIfTI header may include few of the DICOM details, which relate to the image, such as the voxel size, the series description, and/or the like. In a few implementations (e.g. alternate implementations), the second metadata may also eliminate some redundancy in the first metadata. The redundancy can be (1) transmission redundancy where bits of the image are redundantly transmitted regardless of the contents of the image (e.g., when packets are lost in transport), (2) storage redundancy where bits of the image are redundantly written to disk regardless of the contents of the image (e.g., in a redundant array of independent disks (RAID) array), or the like. The transformation from DICOM format to NIfTI format may also result in a reduction of size of the image. For example, a DICOM image with a size of 220 Mb may be converted into a corresponding NIfTI image with a size of 7 Mb. This reduction in size is generally there because DICOM images are often uncompressed, and NIfTI files are often compressed (e.g. gzipped).

The face removal module 128 can receive, at step 7, the NIfTI images and second metadata without PHI and with face along with anonymous IDs from the image transformation module 126. The face removal module 128 can remove the facial data (i.e. faces) from the received NIfTI images and second metadata without PHI and with face along with anonymous IDs to generate NIfTI images and second metadata without PHI and without face along with anonymous IDs. The faces are removed before processing of data to maintain patient privacy while processing of the medical images.

The one or more processors 130 can receive, at step 8, the faceless data (i.e. NIfTI images and second metadata without PHI and without face along with anonymous IDs) from the face removal module 128. The one or more processors 130 can process the received faceless data to generate processed data that does not have either PHI or faces, but includes the anonymous IDs. The processing of faceless data transforms images into data that is useful for clinicians to use in addition to the base images themselves. For example, the processing of faceless data can involve generating a brain atlas, which can be a structural connectivity map of the brain or a functional connectivity map of the brain. The one or more processors 130 can store, at step 9, the processed data in a storage such as a database 132.

Steps 1-9 occur in design-time, which may or may not occur in real-time. Once the database 132 is created or populated in design-time, the database 132 can be queried by the remote computer 108 configured to be operated by a clinician. In some implementations, the transmission of one or more results of the query from the cloud computing system 106, and display of those one or more results by the computer 108, can occur in real-time (e.g. instantaneously after the query is input on the computer 108 prior to transmission of the query to the cloud computing system 106).

The query module 134 can receive, at step 10, a query for real patient data from the computer 108 once the query is input into the computer 108. In response to receipt of the query, the query module 134 can query, at step 11, the gap server 104 for real patient data. More particularly, the query module 134 can encrypt and transmit, at step 11, the query to the communication module 120. The communication module 120 can decrypt the encrypted query and transmit, at step 12, the query to the identifier mapping table 122. In response to the transmission of the query to the identifier mapping table 122, the communication module 120 can retrieve (e.g. receive), at step 13, a reply to the query. The reply to the query can include PHI and anonymous IDs for the patient identified in the query. The communication module 120 can encrypt the reply, and transmit, at step 14, the encrypted reply to the query module 134. The query module 134 can decrypt the reply. The query module 134 can determine the anonymous ID indicated in the reply, and retrieve, at step 15, a portion, of the processed data, that corresponds to that anonymous ID from the database 132. Step 15 can occur after step 14. In other implementations, step 15 can happen before or in parallel with any of steps 11-14. The retrieved processed data does not include PHI or faces, but the PHI is now available within the reply. The query module 134 can separately transmit, at step 16, (a) the queried processed data (which does not include PHI or faces) along with the anonymous ID, and (b) the PHI, to the computer 108. In some implementations, step 16 can occur in real-time (e.g. instantaneously after step 10).

Figure 2:
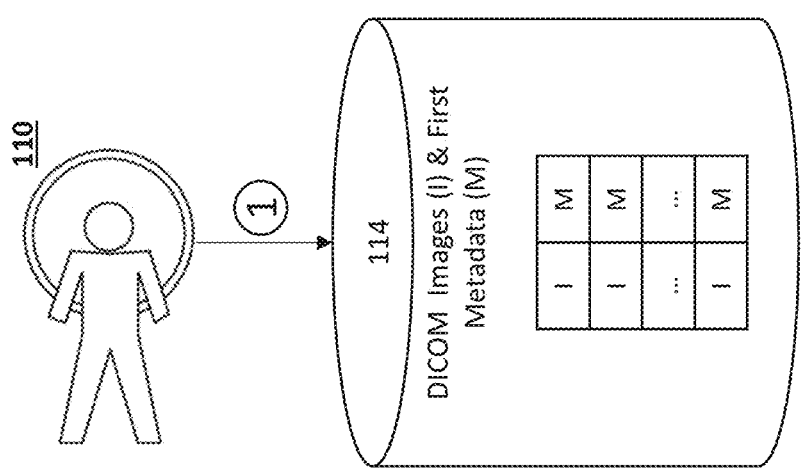
FIG. 2 illustrates a picture archiving and communication system (PACS) system within a hospital information technology (IT) infrastructure to store medical images (e.g. DICOM images) and first metadata.

FIG. 2 illustrates a database 114 within PACS 102 within a hospital information technology (IT) infrastructure to store medical images (e.g. DICOM images, referenced as "I"s) and first metadata (referenced as "M"). First metadata M is metadata associated with each image I. Metadata M for each image I is information that describes that image I. Such metadata M can embedded in the beginning of the image file for that image I as a header, in DICOM tags, or in pixel data related to the DICOM images Is.

Metadata M can include one or more of at least the following: (1) data about the image I, such as image matrix dimensions, the spatial resolution, the pixel depth, the photometric interpretation, or the like, (2) data identifying the imaging device 110, such as make and model of the imaging device 110, location of the imaging device 110, or the like, (3) data indicating how the image I was produced by the imaging device 110, such as parameters related to the pulse sequence used by the imaging device 110, e.g. timing data, flip angle, number of acquisitions by the imaging device 110, and/or (4) PHI, which can be identification data associated with the medical image, such as patient identification by way of name, address, birth date, social security number, medical and laboratory reports, physician name, hospital name, and date of examination.

Figure 3:
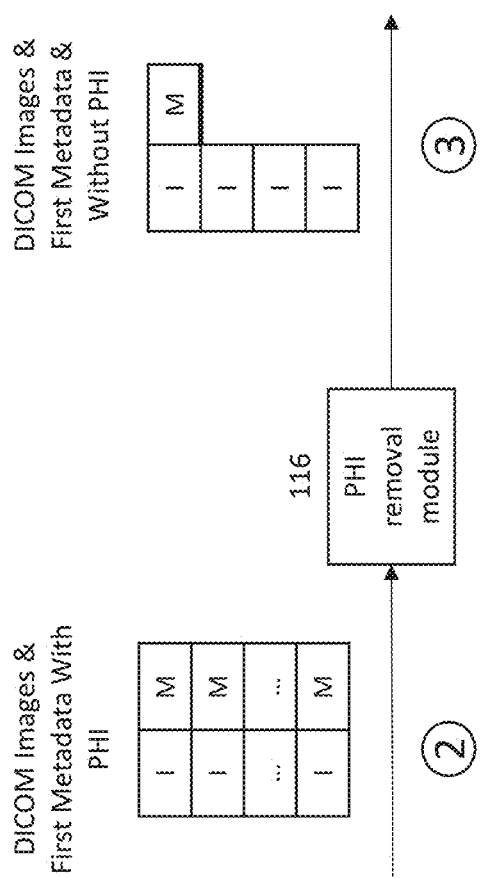
FIG. 3 illustrates removal of PHI by a PHI removal module of a gap server within the hospital IT infrastructure.

FIG. 3 illustrates removal of PHI by a PHI removal module 116 of a gap server 104 within the hospital IT infrastructure. For any image I where the respective metadata M included only PHI, there may be no remaining metadata M for that image I, as shown for some of the images Is.

Figure 4:
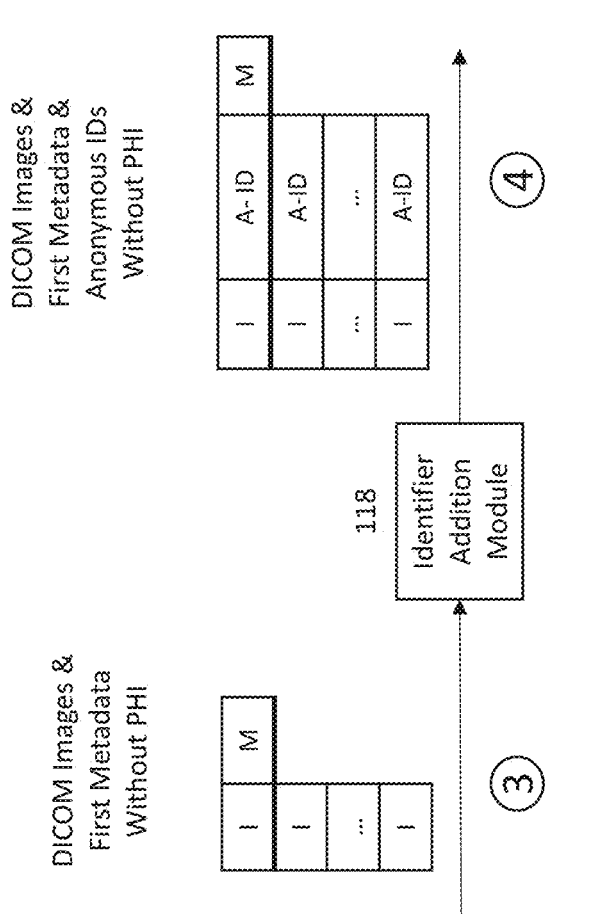
FIG. 4 illustrates addition of anonymous identifiers by an identifier addition module of the gap server within the hospital IT infrastructure.

FIG. 4 illustrates addition of anonymous identifiers A-IDs by an identifier addition module 118 of the gap server 104 within the hospital IT infrastructure. The identifiers (IDs) are used here because the DICOM standard requires values for various IDs, such as a patient ID, a patient name, and/or a few other IDs. A-IDs refer to values used anonymously in place of the real values of such IDs. An example of a table showing conversion from real IDs to A-IDs is below.

| Real IDs | Anonymous IDs |
| --- | --- |
| Patient Name: John Doe | Patient Name: Anonymized 1 (which may not be redacted, but may be anonymized) |
| Patient ID: 34190578 (which can be a medical record number) | Patient ID: [redacted] |
| Study Instance UID: 1.345987.345890.2031 (which can be a unique identifier for the scan session) | Study Instance UID: 2.3.4.5.4101 (which may not be redacted, but may be anonymized) |

Figure 5:
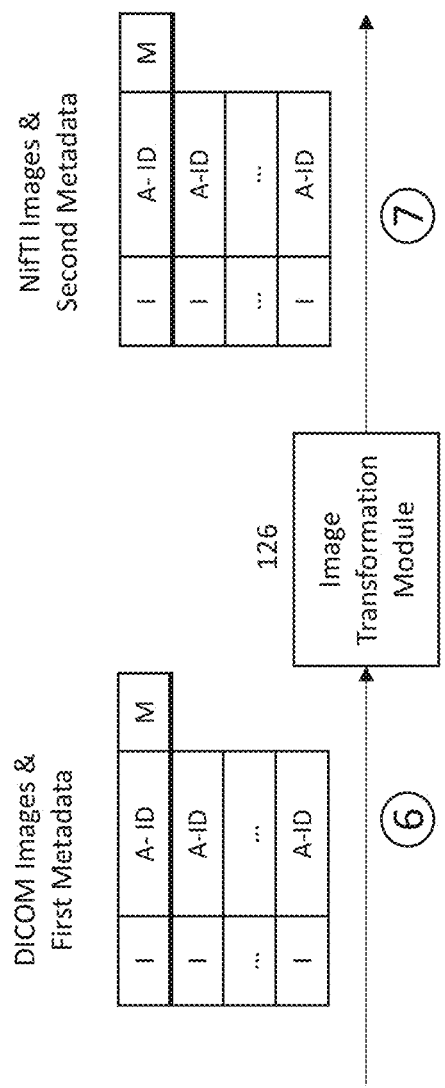
FIG. 5 illustrates transformation from DICOM images and first metadata to NifTI images and second metadata, as performed by an image transformation module within the cloud computing system.

FIG. 5 illustrates transformation from DICOM images and first metadata along with anonymous IDs to NifTI images and second metadata along with anonymous IDs, as performed by an image transformation module 126 within the cloud computing system 106. The second metadata is related to, and created from, the first metadata. The second metadata is created from the first metadata because the NIfTI header is different from the DICOM header, and cannot contain all the data contained in the DICOM header. For example, the DICOM header contains various scan parameters—e.g. .bval file parameters, .bvec file parameters, repetition time, flip angle, and/or the like—that are not saved to the NIfTI file (and these parameters may be extracted into separate files as relevant or needed). The NIfTI header may include few of the DICOM details, which relate to the image, such as the voxel size, the series description, and/or the like. The transformation from DICOM format to NIfTI format may also result in a reduction of size of the image. For example, a DICOM image with a size of 220 Mb may be converted into a corresponding NIfTI image with a size of 7 Mb. This reduction in size is generally there because DICOM images are often uncompressed, and NIfTI files are often compressed (e.g. gzipped).

Figure 6:
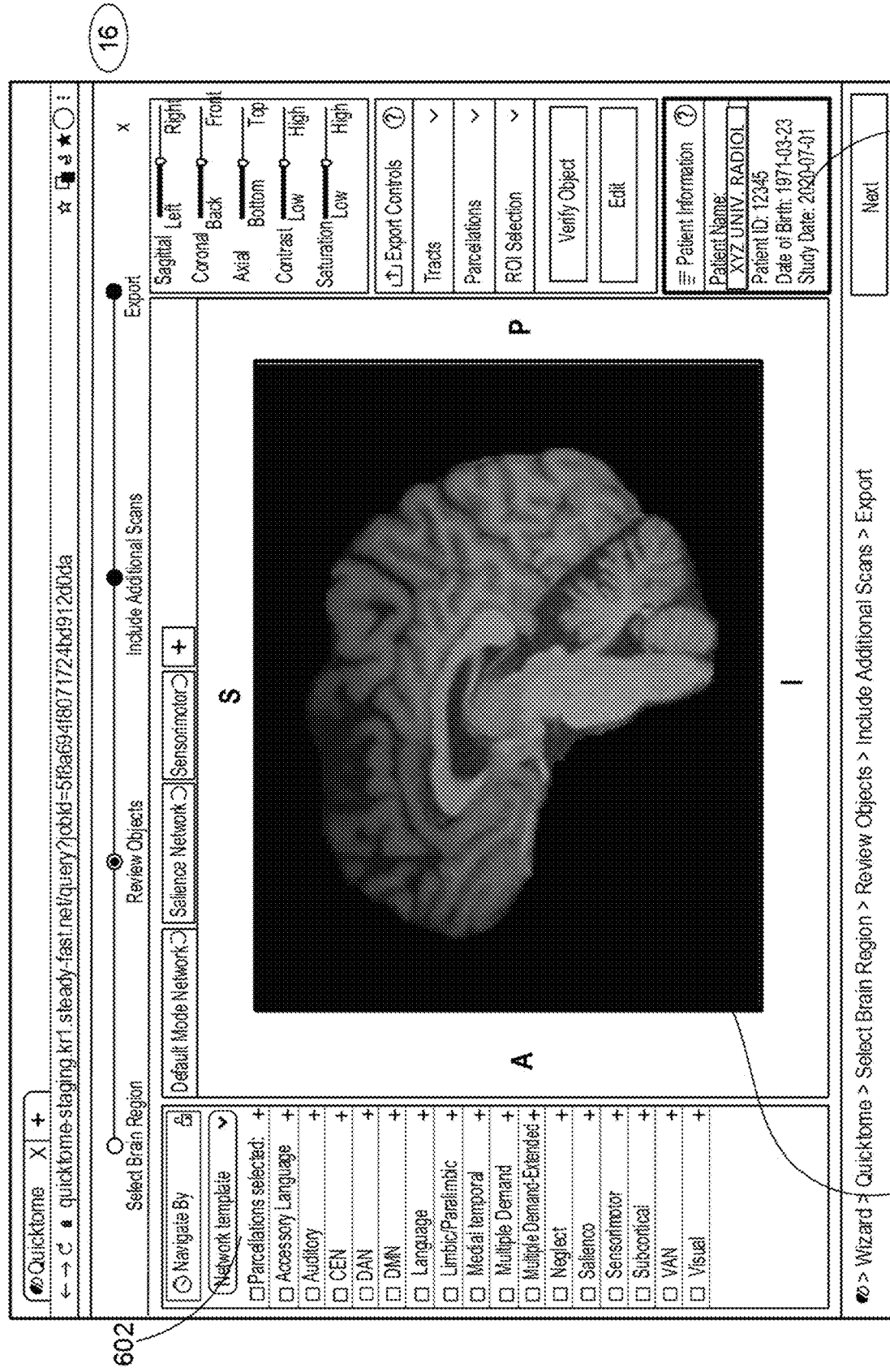
FIG. 6 illustrates the remote computer that displays the medical imaging data that is a result of querying on the remote computer along with PHI for that medical imaging data.

FIG. 6 illustrates an application 602 implemented on the computer 108 that displays the processed medical imaging data that is a result of querying on the computer 108 along with the PHI for that medical imaging data. Further, the clinician can specify particular objects (e.g. by making selections on an application provided on a graphical user interface of the computer 108) that the clinician would like to export to their PACS 102 within the IT network of the hospital where the clinician works. The processed data stored in the database 132 of the cloud computing system 106 does not include PHI or faces. The data provided by the PACS 102 can be most useful to a hospital clinician or staff when the data shows PHI or faces while preserving patient privacy when such data is outside the hospital IT network. A form of PHI attachment is described above. Therefore, the focus is on reattachment of facial data (i.e. face of patient) prior to providing medical imaging data to PACS 102, which displays medical imaging data with faces to a brain navigation system.

The brain navigation system can be configured to display visual representations of the interior of a brain of a patient for clinical analysis and medical intervention, as well as visual representation of physiology of specific portions or objects of the brain (e.g. tracts or parcellations of the brain). Such visual representations can reveal internal structures hidden by the skin and bones, and can be used to diagnose and treat disease.

Figure 7:
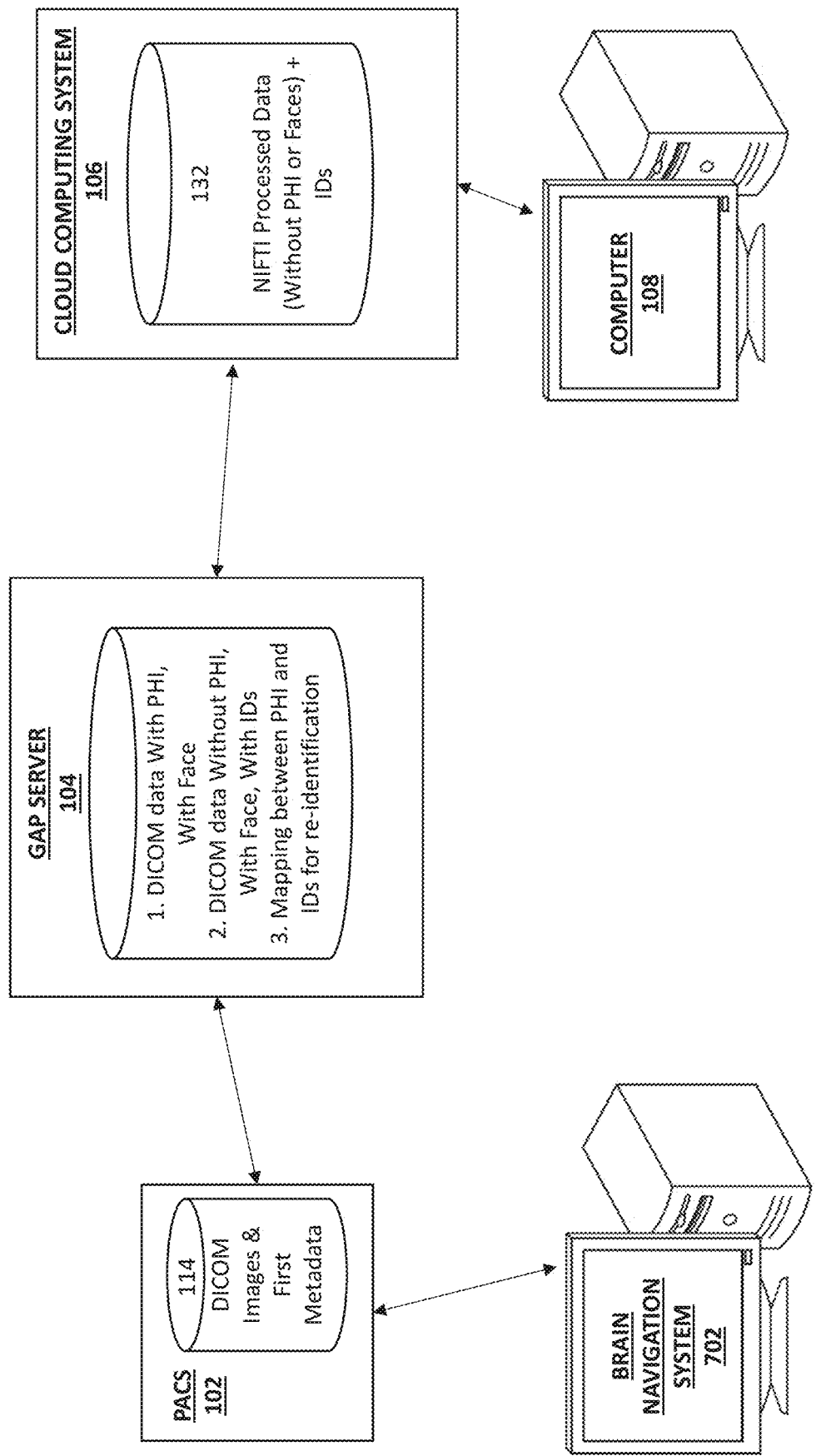
FIG. 7 illustrates some components of the computing landscape of FIG. 1 to show the data present in various computing systems prior to export of medical imaging data to a brain navigation system.

FIG. 7 illustrates a computing system 700 (which includes components of the computing system 100 of FIG. 1) to show the data present in various computing systems prior to transmission of medical imaging data with faces to a brain navigation system 702. The status of this data reflects the design-time stage where the medical imaging data is processed to generate or populate the database 132, as explained above with respect to FIG. 1. The populated data within the database 132 can be queried and/or provided to the brain navigation system 702 in accordance with preferences (e.g. one or more objects) specified by the clinician or a hospital administrator on the computer 108, as explained in greater detail with respect to FIG. 8 below.

The brain navigation system 702 can be a specialized computing system in the hospital IT infrastructure. The brain navigation system 702 may be configured—e.g. by authentication mechanisms such as login using username and/or password, biometric detection, and/or the like—to be used by only authorized individuals, such as clinicians (e.g. doctors, nurses, clinical staff, or the like) or other authorized users (e.g. network administrator, technical staff, or the like) at the hospital. The brain navigation system 702 can be equipped with visualization programs (e.g. by way of installing such visualization programs) that can be linked up with one or more external devices. For example, the brain navigation system 702 can be linked up with one or more external devices (e.g. remote computers) to facilitate a brain surgery.

Although a brain image is useful for a clinician, the clinician can benefit more if the clinician is informed about where the clinician (e.g. surgeon) is about to cut in real-time. The brain navigation system 702 can provide the surgeon with a probe that can help map the image space to the real-world space, such that when the surgeon puts the probe into the head of the patient, an output device (e.g. graphical user interface) of the brain navigation system 702 surgeon can output (e.g. display to the surgeon) where the tip is relative to the virtual objects rendered on the output device.

In some implementations, the brain navigation system 702 may be a device configured to be coupled to the computer 108, either physically or by way of a communication network. In such implementations, the brain navigation system 702 may or may not be connected to the internet, but the computer 108 is connected to the internet.

Figure 8:
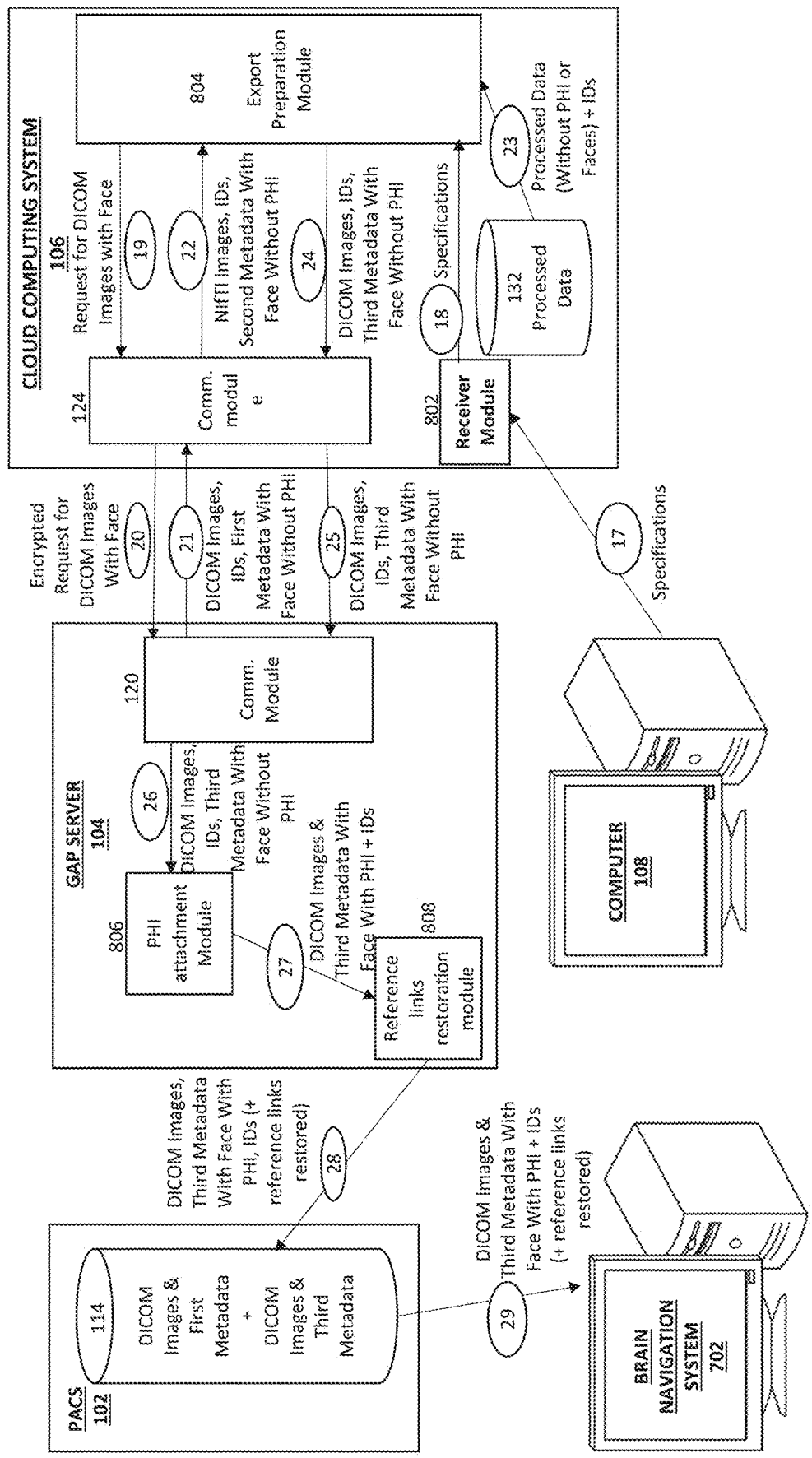
FIG. 8 illustrates export, to the brain navigation system, of medical imaging data that is in accordance with preferences (e.g. one or more objects) specified by the clinician and has reattached the face of the patient.

FIG. 8 illustrates a computing system 800 that transmits, to a brain navigation system 702, medical imaging data—to which patient's face has been reattached—that is in accordance with preferences (e.g. one or more objects) specified by the clinician. The computing system 800 can include PACS 102, gap server 104, cloud computing system 106, computer 108, and a brain navigation system 702. In addition to the components (e.g. modules) noted above with respect to FIG. 1, the gap server 104 and the cloud computing system 106 can include additional modules as shown. For example, the cloud computing system 106 can also include a receiver module 802 and an export preparation module 804, and the gap server 104 can also include a PHI attachment module 806 and a reference links restoration module 808.

The computer 108 can receive, as input on an application on a graphical user interface of the computer 108, specifications for selecting portion of processed data within the database 132. The specifications can be input on the application by a clinician, hospital administrator, or another authorized individual, who may need to be authenticated—e.g. by way of authentication information such as username, password, biometric data, or the like. The specifications can be indicative of objects—e.g. brain tracts and/or brain parcellations—that the clinician, hospital administrator, or other authorized individual desires to export to their PACS 102. A brain tract refers to a bundle of fibers in the nervous system that connects one area to another and usually consists mostly of white matter. A brain parcellation can be a distinct partition in the brain, where such partition can be an area or network that includes multiple discontinuous but closely interacting regions. The clinician may specify such objects (e.g. brain tracts and/or brain parcellations) so as to analyze those specific objects of the brain. The clinician may desire to identify and specify, on the graphical user interface of the computer 108, particular objects on several features, such as local properties of brain tissue, long-range connectivity patterns, structural markers, functional markers, and/or the like.

The receiver module 802 can receive, at step 17, the specifications from the computer 108. The export preparation module 804 can receive, at step 18, the specifications from the receiver module 802. The export preparation module 804 can generate and transmit, at step 19 and to the communication module 124, a request to retrieve DICOM images with face from the gap server 104. The communication module 124 can encrypt and transmit, at step 20, the received request for DICOM images with face to the communication module 120 within the gap server 104. The communication module 120 can decrypt the received request and retrieve, in response, DICOM images with face, but without PHI, along with anonymous IDs from a storage (e.g. database) within the gap server 104. The communication module 120 can encrypt the retrieved data (i.e. DICOM images with face, but without PHI, along with anonymous IDs) to the communication module 124 of the cloud computing system 106.

The communication module 124 can decrypt the encrypted data (i.e. DICOM images with face, but without PHI, along with anonymous IDs) to obtain the DICOM images with face, but without PHI, along with anonymous IDs. The image transformation module 126 (shown in FIG. 1) can transform the DICOM images to NIfTI images with second metadata, but without PHI, along with anonymous IDs. The export preparation module 804 can receive, at step 22 and from the image transformation module 126, the NIfTI images with second metadata, but without PHI, along with anonymous IDs.

The export preparation module 804 can retrieve, at step 23 and from the database 132 storing processed data, specific processed data, without PHI or faces, along with anonymous IDs. The export preparation module 804 can use the data received at steps 22 and 23 to generate DICOM images and third metadata with face, but without PHI, along with the anonymous IDs. The third metadata refers to data in the DICOM header obtained by converting the data available about the scan from the NIfTI files (and additional files available at this time). The third metadata is different from other metadata (which included data in the original DICOM header) because the original DICOM files are not being recreated, and the DICOM images being created by the export preparation module 804 are generally different from the original DICOM images (with, generally, the only same thing in original DICOM images and the DICOM images being created by the export preparation module 804 being anonymized IDs and the image data (containing the face). The rest of the metadata in DICOM images being created by the export preparation module 804 pertains to the objects that are being encoding into outputs. In the example of brain parcellations, the face is available and the image data can be changed to mark where the selected brain parcellations are, and the metadata indicates to a viewing application how to visualize the data (e.g. whether the image data should be read as a color image with the parcellation colored red and the backdrop being grayscale).

Thus, the export preparation module 804 performs export preparation, which includes the following: (a) put the face in the image data, (b) where applicable, modify the image data to mark where the objects are, (c) add the anonymized IDs in the header, (d) add header information to specify (i) data that has been encoded, (ii) version of the software that was used to create the outputs, (iii) any reference links there may be with other DICOM sets in the same package, (iv) how to interpret the image, and/or the like.

The communication module 124 can receive, at step 24 and from the export preparation module 804, the DICOM images and third metadata with face, but without PHI, along with the anonymous IDs. The communication module 124 can encrypt the received data (i.e. DICOM images and third metadata with face, but without PHI, along with the anonymous IDs). The communication module 124 can transmit, at step 25, the encrypted data (i.e. encrypted DICOM images and third metadata with face, but without PHI, along with the anonymous IDs) to the communication module 120.

The communication module 120 can decrypt the encrypted data (i.e. encrypted DICOM images and third metadata with face, but without PHI, along with the anonymous IDs) received at step 25. The communication module 120 can transmit, at step 26, the decrypted data (i.e. DICOM images and third metadata with face, but without PHI, along with the anonymous IDs) to the PHI attachment module 806.

The PHI attachment module 806 can retrieve, from a storage (e.g. database) within the gap server 106, PHI corresponding to the anonymous IDs. The PHI attachment module 806 can attach (e.g. generate a mapping) the PHI to the data received at step 26 to generate DICOM images and third metadata with face and PHI along with the anonymous IDs.

The reference links restoration module 808 can receive, at step 27 from the PHI attachment module 26, the DICOM images and third metadata with face and PHI along with the anonymous IDs. The reference links restoration module 808 can use the data received at step 27 to restore (e.g. fix) previously-broken reference links.

The following explains reference links, location where the reference links reside, reason for breaking of reference links, and actions performed by the reference links restoration module 808 to restore or fix those reference links. A reference link can be an identifier referenced to visualize specific data. For instance, to visualize some DICOM objects, a reference link (e.g. reference image) needs to be provided. For example, to view DICOM set A, reference links in the form of references ID B-123 may need to be provided. The reference link may cause viewing of DICOM set A with DICOM set B. Without the reference link, DICOM set A may not be displayed by a viewer because the viewer is unable to recognize or find DICOM set B. The reference links reside in the third metadata of the DICOM header of the outputs.

The reference links are broken because by DICOM convention, no two DICOM sets (which can be referred to as series) can have the same series instance unique identifiers (UIDs). In re-identifying the DICOM sets, a new series instance UID must be created for each new series created to go along with the original patient and study instance UIDs. Because the reference links were built on the cloud computing system 106 using the previous series instance UID, they are required to be modified to the new series instance UID.

The reference links use private tags, which are not modified by the re-identification module, to create the mapping between the previous and the new series instance UIDs and modify the appropriate tags to point to the new ones.

One example where reference links are broken and then restored is presented below.

| On Cloud | After re-identification | After reference fixing |
| --- | --- | --- |
| DICOM Set A Study UID = 1.2.3.4.5 (anonymous) Series UID = 1.2.3.4.5.201 Reference link to DICOM set B: Series UID = 1.2.3.4.5.202 | DICOM Set A Study UID = 9.8.7.6.5 (original) Series UID = 9.8.7.6.5.901 (new) Reference link to DICOM set B broken: Series UID = 1.2.3.4.5.202 | DICOM set A Study UID = 9.8.7.6.5 (original) Series UID = 9.8.7.6.5.901 (new) Reference link (links to DICOM set B restored): Series UID = 9.8.7.6.5.902 |
| DICOM set B Study UID = 1.2.3.4.5 (anonymous) Series UID = 1.2.3.4.5.202 | DICOM set B DICOM set A Study UID = 9.8.7.6.5 Series UID = 9.8.7.6.5.902 | DICOM set B Study UID = 9.8.7.6.5 Series UID = 9.8.7.6.5.902 |

The reference links restoration module 808 can transmit, at step 28, the DICOM images and third metadata with face and PHI along with the anonymous IDs, where reference links have been restored, to the PACS 102.

PACS 102 can store the data received at step 28 (i.e. DICOM images and third metadata with face and PHI along with the anonymous IDs, where reference links have been restored) in the storage 114. PACS 102 can transmit, at step 29, the data received at step 28 (i.e. DICOM images and third metadata with face and PHI along with the anonymous IDs, where reference links have been restored) to the brain navigation system 702.

Figure 9:
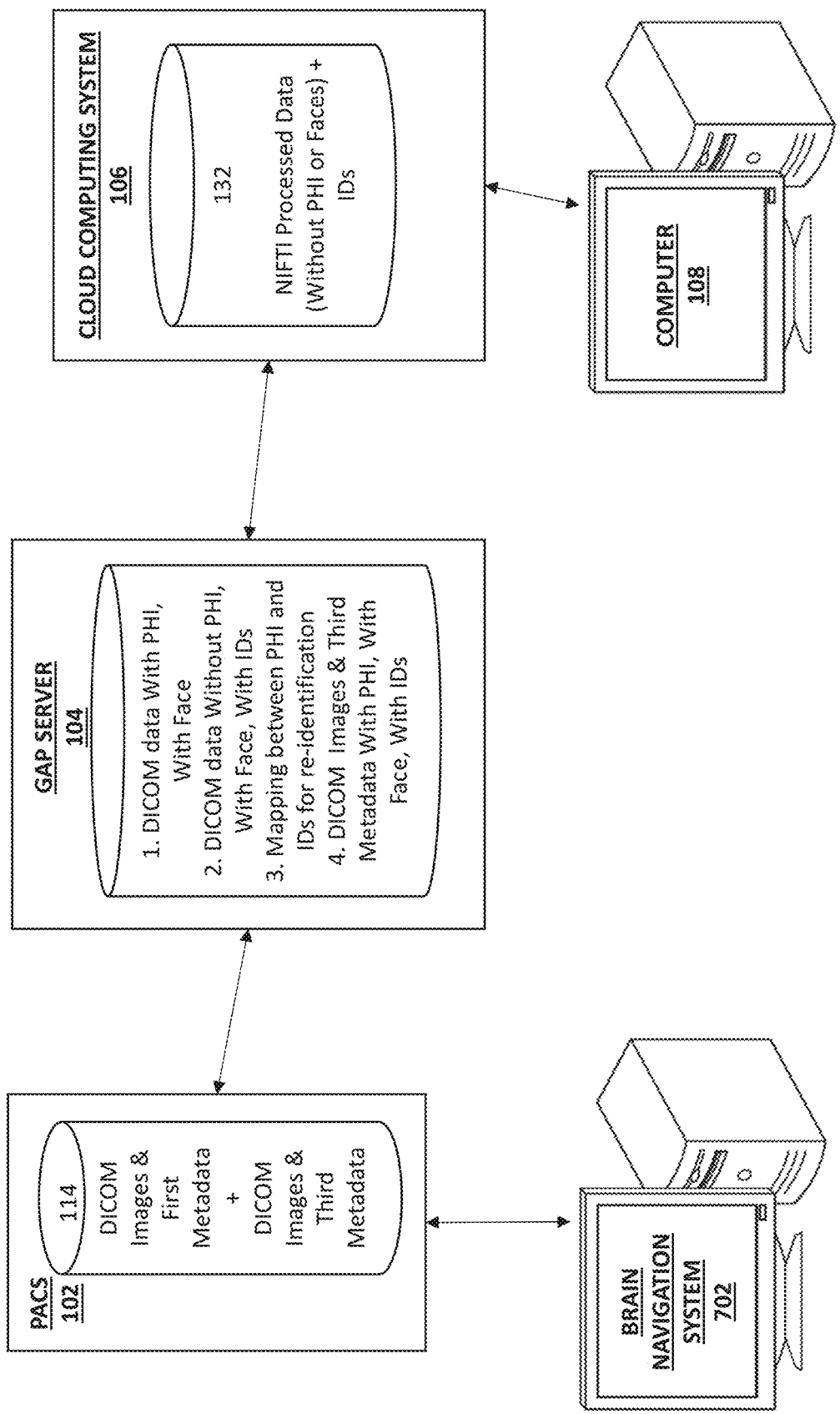
FIG. 9 illustrates the components of the computing landscape of FIG. 7 to show the data present in various computing systems after the export of medical imaging data to the brain navigation system.

FIG. 9 illustrates the components of the computing system of FIG. 7 to show the data present in PACS 102, gap server 104, and cloud computing system 106 after the export of medical imaging data to the brain navigation system 702.

Figure 10:
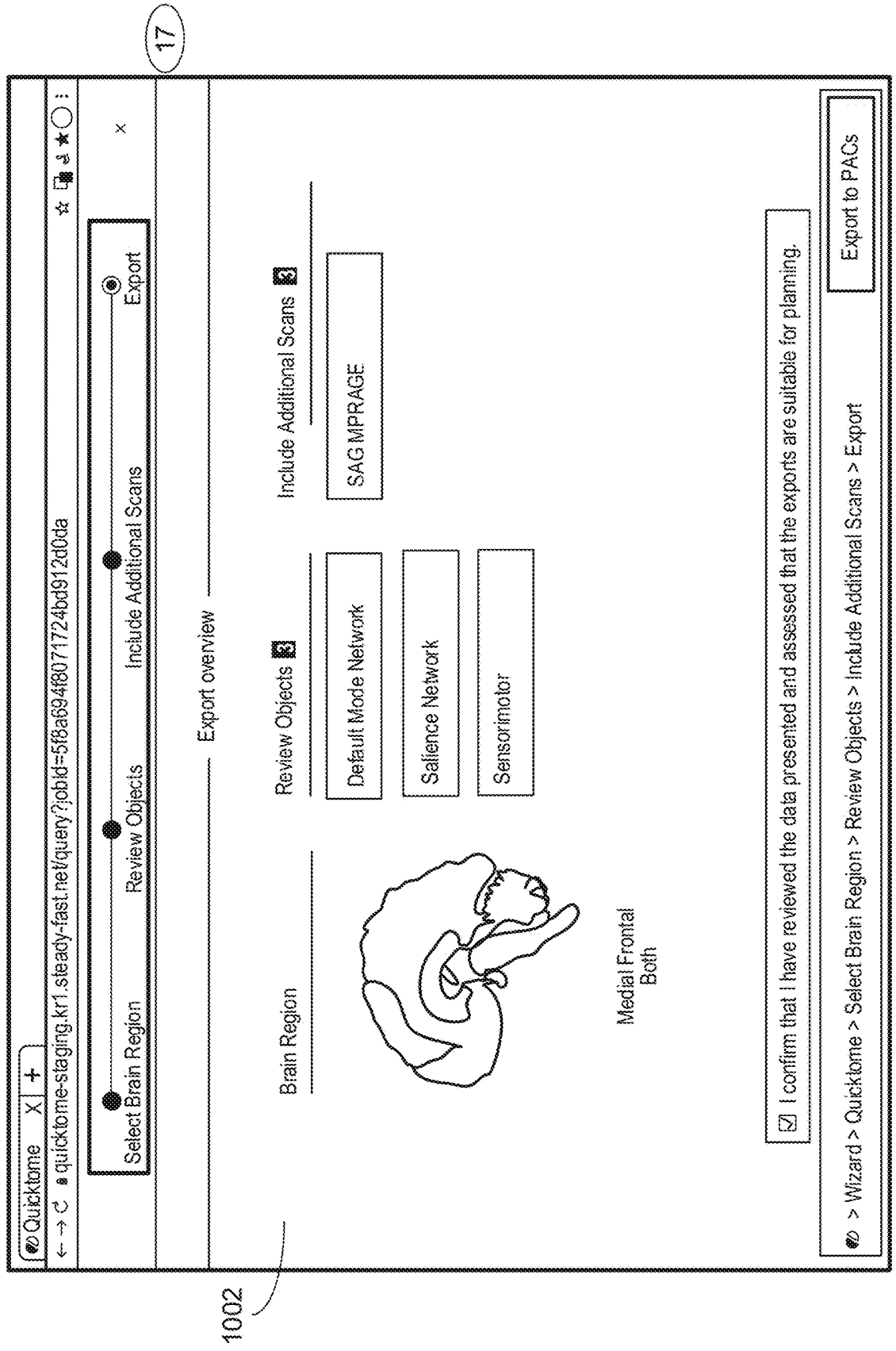
FIG. 10 illustrates an application on a graphical user interface of the remote computer that allows the clinician to specify one or more objects (e.g. by way of selection from multiple objects) to be exported to the brain navigation system.

FIG. 10 illustrates an application 1002 on a graphical user interface of the computer 108 that allows the clinician or another authorized individual to specify (e.g. by way of selection from multiple objects) one or more objects (e.g. tracts and/or parcellations) to be exported to the brain navigation system 702. The application 1002 is shown as a browser. In other implementations, the application 1002 can be a native application installed on the computer 108. Generally, the application implemented on any computing device described herein can be in the form of a browser or a native application.

Figure 11:
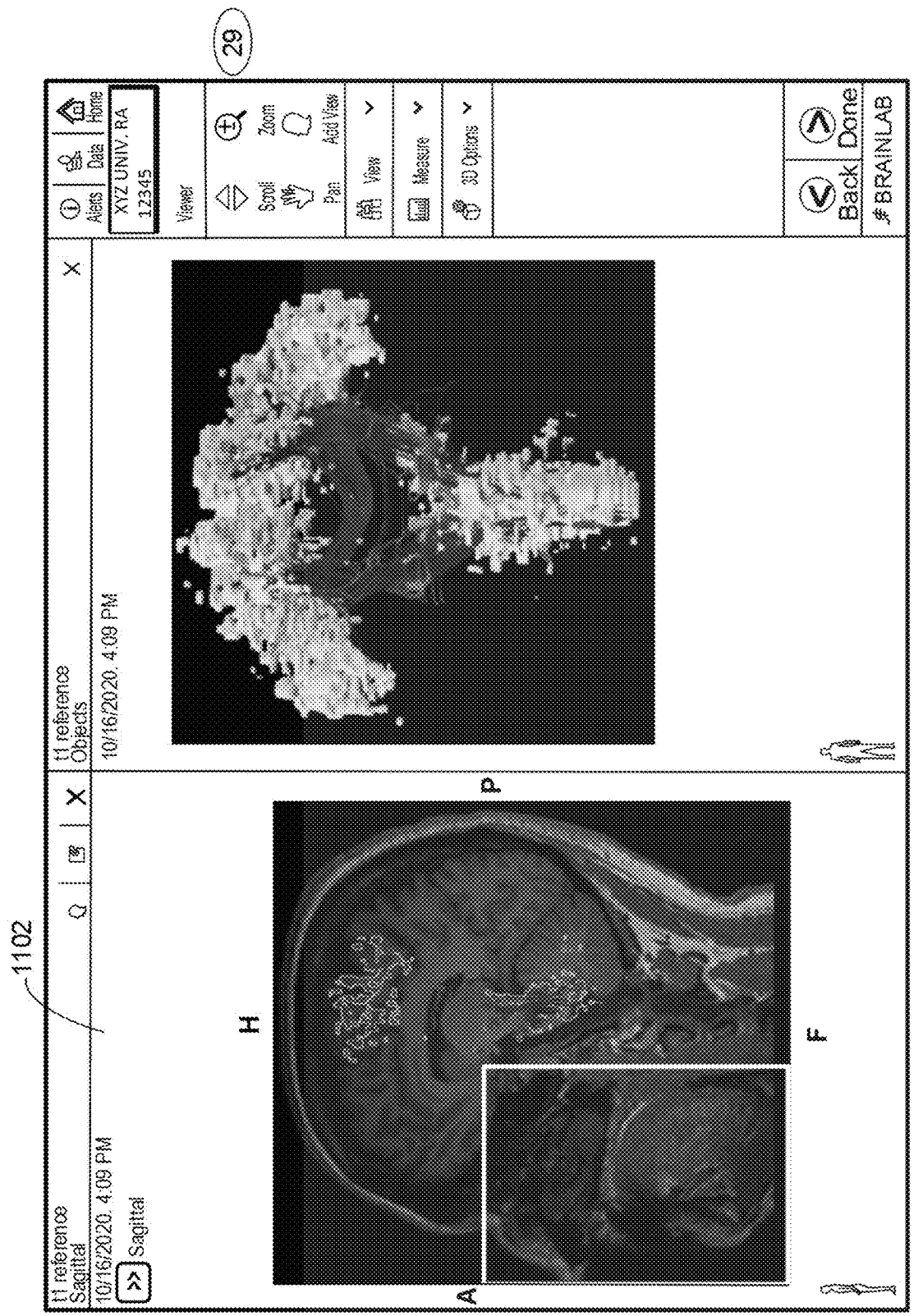
FIG. 11 illustrates another application on a graphical user interface of the brain navigation system that displays the medical imaging data in accordance with the one or more objects specified by the clinician.

FIG. 11 illustrates an application 1102 on a graphical user interface of the brain navigation system 702 that displays an analysis of the brain in accordance with specifications (e.g. objects, such as tracts and parcellations) provided by the clinician or another authorized individual at step 17. For example, the brain navigation system 702 displays an analysis of the brain along tracts and parcellations specified by the clinician at step 17. The displayed analysis can include DICOM images and third metadata with face and PHI along with the anonymous IDs, where reference links have been restored.

Figure 12:
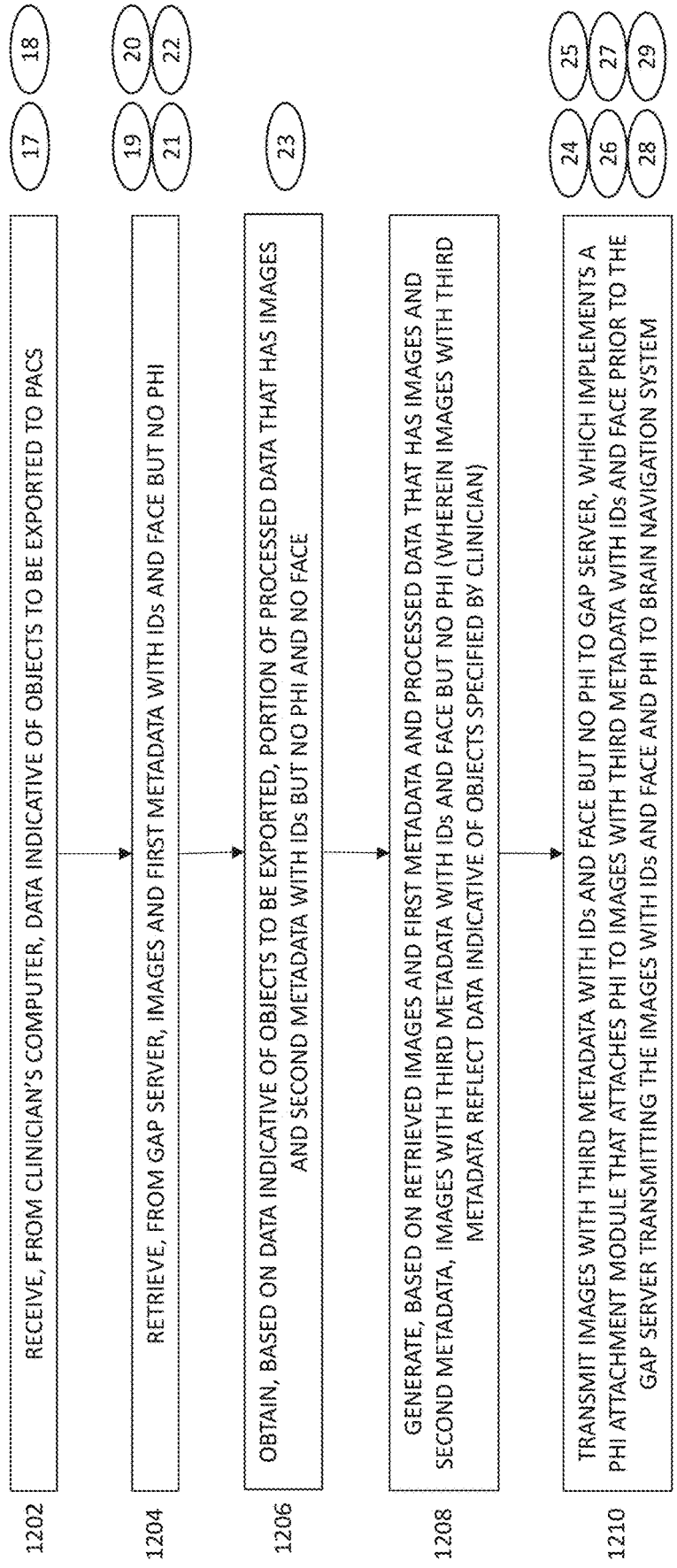
FIG. 12 illustrates a process of generating and exporting, to the brain navigation system, of medical imaging data that is in accordance with preferences (e.g. one or more objects) specified by the clinician and has reattached the face of the patient.

FIG. 12 illustrates a process of generating, and exporting to the brain navigation system, medical imaging data that is in accordance with specifications (e.g. one or more objects) provided by the clinician and has reattached the face of the patient. The cloud computing system 106 can receive, at 1202 from a remote computer 108, data indicative of objects (e.g. tracts and parcellations for brain images) specified by a clinician and to be exported to PACS 102 (e.g. see steps 17 and 18 described above). The cloud computing system 106 can retrieve, at 1204 from the gap server 104, images and first metadata with anonymous identifiers and face but no PHI (e.g. see steps 19, 20, 21 and 22 described above). The cloud computing system 106 can obtain, at 1206 and based on data indicative of objects to be exported, a portion of processed data that has images and second metadata with anonymous IDs but no PHI and no face (e.g. see step 23 described above). The cloud computing system 106 can generate, at 1208 and based on retrieved images and first metadata as well as processed data that has images and second metadata, images with third metadata with IDs and face but no PHI. The images with third metadata reflect data indicative of objects specified by clinician.

The cloud computing system 106 can transmit, at 1210, images with third metadata with IDs and face but no PHI to gap server 104 (e.g. see steps 24 and 25 described above). The gap server 104 can implement a PHI attachment module 806 that attaches PHI to images with third metadata with IDs and face (e.g. see steps 26 and 27 described above). Subsequently, the gap server 104 can transmit the images with IDs and face and PHI to PACS 102 (e.g. see step 28 described above). PACS 102 can transmit the images with IDs and face and PHI to the brain navigation system 702 (e.g. see step 29 described above).

FIGS. 13A and 13B show examples of a computing device 1300 and a mobile computing device 1350, respectively, which can be used as data processing apparatuses to implement the techniques described here. In some implementations, each of PACS 102, gap server 104, cloud computing system 106, computer 108, and brain navigation system 702 may include, be a part of, or use one or more of the computing device 1300 or the mobile computing device 1350. The computing device 1300 is intended to represent various forms of digital computers, such as laptops, desktops, workstations, personal digital assistants, servers, blade servers, mainframes, and other appropriate computers. The mobile computing device 1350 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1300 includes a processor 1302, a memory 1304, a storage device 1306, a high-speed interface 1308 connecting to the memory 1304 and multiple high-speed expansion ports 1310, and a low-speed interface 1312 connecting to a low-speed expansion port 1314 and the storage device 1306. Each of the processor 1302, the memory 1304, the storage device 1306, the high-speed interface 1308, the high-speed expansion ports 1310, and the low-speed interface 1312, are interconnected using various busses, and may be mounted on a common motherboard or in other manners as appropriate. The processor 1302 can process instructions for execution within the computing device 1300, including instructions stored in the memory 1304 or on the storage device 1306 to display graphical information for a GUI on an external input/output device, such as a display 1316 coupled to the high-speed interface 1308. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1304 stores information within the computing device 1300. In some implementations, the memory 1304 is a volatile memory unit or units. In some implementations, the memory 1304 is a non-volatile memory unit or units. The memory 1304 may also be another form of computer-readable medium, such as a magnetic or optical disk.

The storage device 1306 is capable of providing mass storage for the computing device 1300. In some implementations, the storage device 1306 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1302), perform one or more methods, such as those described above. The instructions can also be stored by one or more storage devices such as computer- or machine-readable mediums (for example, the memory 1304, the storage device 1306, or memory on the processor 1302).

The high-speed interface 1308 manages bandwidth-intensive operations for the computing device 1300, while the low-speed interface 1312 manages lower bandwidth-intensive operations. Such allocation of functions is an example only. In some implementations, the high-speed interface 1308 is coupled to the memory 1304, the display 1316 (e.g., through a graphics processor or accelerator), and to the high-speed expansion ports 1310, which may accept various expansion cards (not shown). In the implementation, the low-speed interface 1312 is coupled to the storage device 1306 and the low-speed expansion port 1314. The low-speed expansion port 1314, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1300 may be implemented in a number of different forms, as shown in the figure. For example, it may be implemented as a standard server 1320, or multiple times in a group of such servers. In addition, it may be implemented in a personal computer such as a laptop computer 1322. It may also be implemented as part of a rack server system 1324. Alternatively, components from the computing device 1300 may be combined with other components in a mobile device (not shown), such as a mobile computing device 1350. Each of such devices may contain one or more of the computing device 1300 and the mobile computing device 1350, and an entire system may be made up of multiple computing devices communicating with each other.

The mobile computing device 1350 includes a processor 1352, a memory 1364, an input/output device such as a display 1354, a communication interface 1366, and a transceiver 1368, among other components. The mobile computing device 1350 may also be provided with a storage device, such as a micro-drive or other device, to provide additional storage. Each of the processor 1352, the memory 1364, the display 1354, the communication interface 1366, and the transceiver 1368, are interconnected using various buses, and several of the components may be mounted on a common motherboard or in other manners as appropriate.

The processor 1352 can execute instructions within the mobile computing device 1350, including instructions stored in the memory 1364. The processor 1352 may be implemented as a chipset of chips that include separate and multiple analog and digital processors. The processor 1352 may provide, for example, for coordination of the other components of the mobile computing device 1350, such as control of user interfaces, applications run by the mobile computing device 1350, and wireless communication by the mobile computing device 1350.

The processor 1352 may communicate with a user through a control interface 1358 and a display interface 1356 coupled to the display 1354. The display 1354 may be, for example, a TFT (Thin-Film-Transistor Liquid Crystal Display) display or an OLED (Organic Light Emitting Diode) display, or other appropriate display technology. The display interface 1356 may include appropriate circuitry for driving the display 1354 to present graphical and other information to a user. The control interface 1358 may receive commands from a user and convert them for submission to the processor 1352. In addition, an external interface 1362 may provide communication with the processor 1352, so as to enable near area communication of the mobile computing device 1350 with other devices. The external interface 1362 may provide, for example, for wired communication in some implementations, or for wireless communication in other implementations, and multiple interfaces may also be used.

The memory 1364 stores information within the mobile computing device 1350. The memory 1364 can be implemented as one or more of a computer-readable medium or media, a volatile memory unit or units, or a non-volatile memory unit or units. An expansion memory 1374 may also be provided and connected to the mobile computing device 1350 through an expansion interface 1372, which may include, for example, a SIMM (Single In Line Memory Module) card interface. The expansion memory 1374 may provide extra storage space for the mobile computing device 1350, or may also store applications or other information for the mobile computing device 1350. Specifically, the expansion memory 1374 may include instructions to carry out or supplement the processes described above, and may include secure information also. Thus, for example, the expansion memory 1374 may be provide as a security module for the mobile computing device 1350, and may be programmed with instructions that permit secure use of the mobile computing device 1350. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1352), perform one or more methods, such as those described above. The instructions can also be stored by one or more storage devices, such as one or more computer- or machine-readable mediums (for example, the memory 1364, the expansion memory 1374, or memory on the processor 1352). In some implementations, the instructions can be received in a propagated signal, for example, over the transceiver 1368 or the external interface 1362.

The mobile computing device 1350 may communicate wirelessly through the communication interface 1366, which may include digital signal processing circuitry where necessary. The communication interface 1366 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1368 using a radio-frequency. In addition, short-range communication may occur, such as using a Bluetooth, WiFi, or other such transceiver (not shown). In addition, a GPS (Global Positioning System) receiver module 1370 may provide additional navigation- and location-related wireless data to the mobile computing device 1350, which may be used as appropriate by applications running on the mobile computing device 1350.

The mobile computing device 1350 may also communicate audibly using an audio codec 1360, which may receive spoken information from a user and convert it to usable digital information. The audio codec 1360 may likewise generate audible sound for a user, such as through a speaker, e.g., in a handset of the mobile computing device 1350. Such sound may include sound from voice telephone calls, may include recorded sound (e.g., voice messages, music files, etc.) and may also include sound generated by applications operating on the mobile computing device 1350.

The mobile computing device 1350 may be implemented in a number of different forms, as shown in the figure. For example, it may be implemented as a cellular telephone 1380. It may also be implemented as part of a smart-phone 1382, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., an OLED (organic light emitting diode) display or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the computing system can be cloud based and/or centrally processing data. In such case anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

Although a few variations have been described in detail above, other modifications are possible. For example, the logic flows described herein may not require the particular order shown (e.g. order of steps described herein), or sequential order (e.g. sequential order of steps described herein), to achieve desirable results. Other implementations may be in the following claims.

The invention claimed is:

1. A method comprising:
receiving, by a cloud computing system from a gap server, brain image data including a) face data and b) first brain image metadata including an anonymous identifier and not otherwise including personal health information (PHI);
removing the face data, by the cloud computing system, from the brain image data to produce faceless brain image data;
processing, by the cloud computing system, the faceless brain image data to produce processed faceless brain image data,
receiving, by the cloud computing system and from a remote computer, data specifying selected brain imaging objects selected by a user;
generating, by the cloud computing system, responsive brain image data based in part on the processed faceless brain image data and the selected brain imaging objects; and
taking action based on the responsive brain image data.

2. The method of claim 1, wherein the gap server implements a PHI attachment module that attaches PHI to the brain images, wherein the gap server transmits the brain images with anonymous identifiers and face data and PHI to a picture archiving and communication system (PACS).

3. The method of claim 2, wherein the PACS transmits the brain images with the anonymous identifiers and the face data and PHI to a brain navigation system.

4. The method of claim 1, wherein the method further comprises
receiving encrypted data indicative of selected brain imaging objects; and
decrypting the received encrypted data prior to the receiving of the brain images and the first brain image metadata from the gap server.

5. The method of claim 4, wherein the data indicative of the selected brain imaging objects comprises one or more of a tract or a parcellation selected from a plurality of objects.

6. The method of claim 1, wherein the generating responsive brain image data comprises:
attaching face data to the brain image in a temporary storage of the cloud computing system.

7. The method of claim 1, wherein the cloud computing system prevents the PHI or the face data from being saved in a database of the cloud computing system.

8. The method of claim 1, wherein taking an action comprises transmitting, by the cloud computing system, the responsive brain image data for display to a user.

9. A system comprising:
one or more computers and one or more storage devices on which are stored instructions that are operable, when executed by the one or more computers, to cause the one or more computers to perform operations comprising:
receiving, by a cloud computing system from a gap server, brain image data including a) face data and b) first brain image metadata including an anonymous identifier and not otherwise including personal health information (PHI);
removing the face data, by the cloud computing system, from the brain image data to produce faceless brain image data;
processing, by the cloud computing system, the faceless brain image data to produce processed faceless brain image data,
receiving, by the cloud computing system and from a remote computer, data specifying selected brain imaging objects selected by a user;
generating, by the cloud computing system, responsive brain image data based in part on the processed faceless brain image data and the selected brain imaging objects; and
taking action based on the responsive brain image data.

10. The system of claim 9, wherein the gap server implements a PHI attachment module that attaches PHI to the brain images, wherein the gap server transmits the brain images with anonymous identifiers and face data and PHI to a picture archiving and communication system (PACS).

11. The system of claim 10, wherein the PACS transmits the brain images with the anonymous identifiers and the face data and PHI to a brain navigation system.

12. The system of claim 9, wherein the method further comprises
receiving encrypted data indicative of selected brain imaging objects; and
decrypting the received encrypted data prior to the receiving of the brain images and the first brain image metadata from the gap server.

13. The system of claim 12, wherein the encrypted data indicative of the selected brain imaging objects comprises one or more of a tract or a parcellation selected from a plurality of objects.

14. The system of claim 9, wherein the generating responsive brain image data comprises:
attaching face data to the brain image in a temporary storage of the cloud computing system.

15. The system of claim 9, wherein the cloud computing system prevents the PHI or the face data from being saved in a database of the cloud computing system.

16. The system of claim 9, wherein taking an action comprises transmitting, by the cloud computing system, the responsive brain image data for display to a user.

17. One or more non-transitory computer program products storing instructions that, when executed by at least one programmable processor, cause the at least one programmable processor to perform operations comprising:
receiving, by a cloud computing system from a gap server, brain image data including a) face data and b) first brain image metadata including an anonymous identifier and not otherwise including personal health information (PHI);
removing the face data, by the cloud computing system, from the brain image data to produce faceless brain image data;
processing, by the cloud computing system, the faceless brain image data to produce processed faceless brain image data, receiving, by the cloud computing system and from a remote computer, data specifying selected brain imaging objects selected by a user;

generating, by the cloud computing system, responsive brain image data based in part on the processed faceless brain image data and the selected brain imaging objects; and taking action based on the responsive brain image data.

18. The one or more non-transitory computer program products of claim 17, wherein the gap server implements a PHI attachment module that attaches PHI to the brain images, wherein the gap server transmits the brain images with anonymous identifiers and face data and PHI to a picture archiving and communication system (PACS).

19. The one or more non-transitory computer program products of claim 18, wherein the PACS transmits the brain images with the anonymous identifiers and the face data and PHI to a brain navigation system.

20. The one or more non-transitory computer program products of claim 18, wherein the operations further comprise:

receiving encrypted data indicative of selected brain imaging objects; and decrypting the received encrypted data prior to the receiving of the brain images and the first brain image metadata from the gap server.

* * * * *